United States Patent [19]

Gilbreath, Jr. et al.

[11] Patent Number: 5,660,794

[45] Date of Patent: Aug. 26, 1997

[54] LIGHT STABILITY CHAMBER

[75] Inventors: Cooper Gordon Gilbreath, Jr., Mays Landing; Philip Francis Naimoli, Jr., Blackwood; James John Donaghue, Nesco, all of N.J.

[73] Assignee: American Home Products Corporation, Madison, N.J.

[21] Appl. No.: 590,232

[22] Filed: Jan. 23, 1996

[51] Int. Cl.$^6$ .................................................. G01N 17/00
[52] U.S. Cl. .................. 422/68.1; 73/865.6; 250/492.1; 312/209; 422/104
[58] Field of Search .............. 422/68.1, 99, 104, 422/24; 73/866, 865.6; 250/522.1, 492.1; 435/292.1; 312/209, 225, 223.5

[56] References Cited

U.S. PATENT DOCUMENTS

| | | | |
|---|---|---|---|
| 3,433,949 | 3/1969 | Truban | 250/51 |
| 3,686,940 | 8/1972 | Kockott | 73/150 |
| 4,011,456 | 3/1977 | Bredewater et al. | 250/492.1 |
| 4,760,748 | 8/1988 | Katayanagi et al. | 73/865.6 |
| 4,874,952 | 10/1989 | Arnaud et al. | 250/492.1 |

OTHER PUBLICATIONS

Technical Manual for Forma Scientific Incubator Model #3918—Manual #7023918—Box 649, Marietta, Ohio.

*Primary Examiner*—Jill Warden
*Assistant Examiner*—Jan M. Ludlow
*Attorney, Agent, or Firm*—S. H. Flynn

[57] ABSTRACT

There is provided a light stability chamber for determining the stability to light of samples, for example, of pharmaceuticals in order to determine the shelf life of the samples by subjecting the samples to light from all angles.

6 Claims, 2 Drawing Sheets

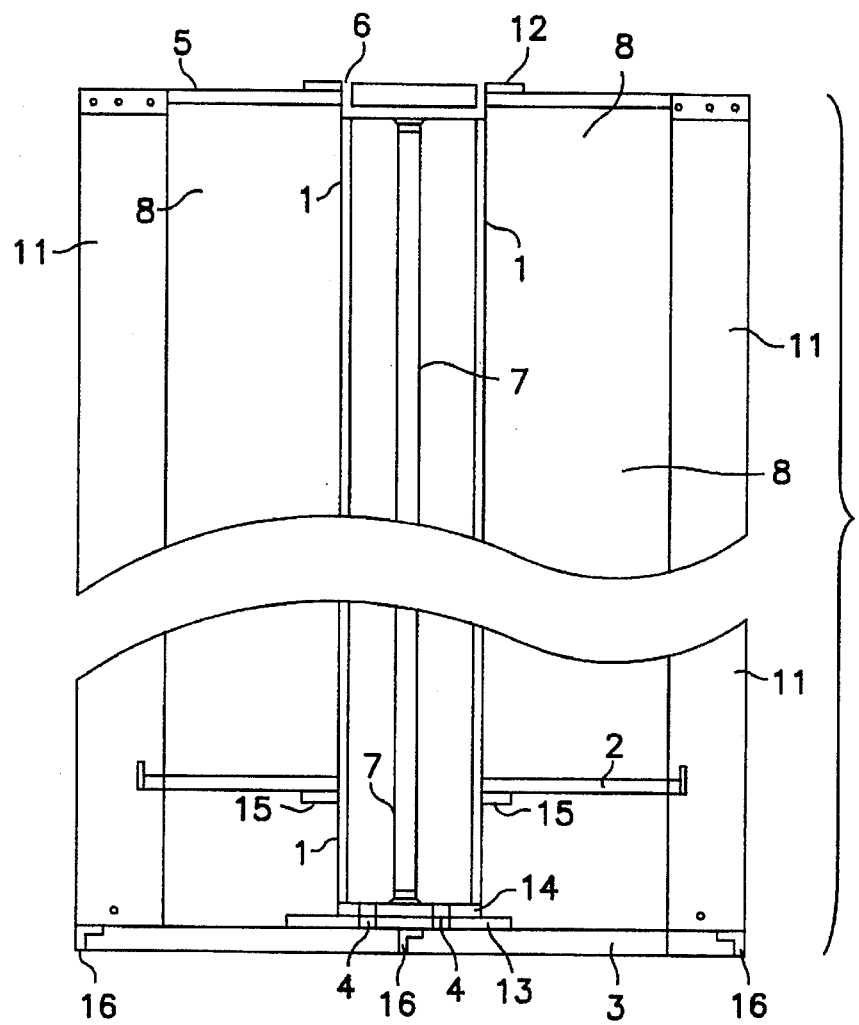
FIG. 2
FIG. 3
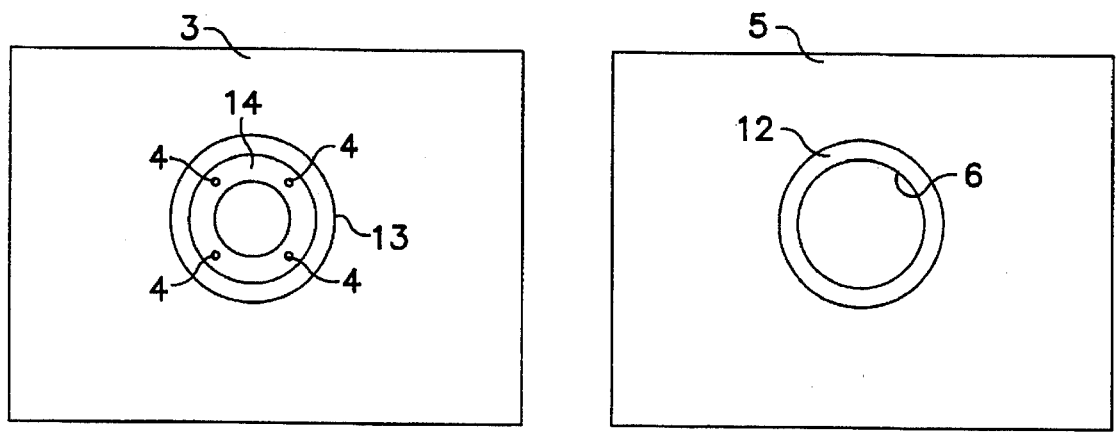
FIG. 4
FIG. 5

LIGHT STABILITY CHAMBER

BACKGROUND OF THE INVENTION

This invention relates in general to a light stability apparatus. More particularly this invention relates to an apparatus in which the light sensitivity of various materials, such as pharmaceutically active compounds, is determined by simultaneous exposure of the material to artificial light from all angles, i.e. the materials are bathed in light.

Most pharmaceutical preparations, both solid and liquid, are required by the Food and Drug Administration of the United States Department of Health and Human Services (hereinafter the FDA) to provide in their labeling an "expiration date" after which the preparation may not have the listed potency due to degradation of the active ingredient caused by light or heat. This expiration date is usually found stamped on the preparation labeling or on the package itself.

The expiration date of, for example, a pharmaceutical preparation is most often established by stability testing using guidelines or standards set by the FDA. The stability testing required by the FDA to establish the expiration date of a preparation usually involves light, heat and humidity testing under controlled conditions set forth in FDA rules.

Stability testing is also required by the FDA for New Drug Application (NDA) filing and for ANDA filing and approval. The FDA has recently published a guideline entitled "Stability Testing of New Drug Substances and Products" prepared under the auspices of the International Conference on Harmonization of Technical Requirements for Registration of Pharmaceuticals for Human Use (ICH). These guidelines for stability testing appear to require more stringent stability testing than before.

Various manufacturers provide the pharmaceutical industry with cabinets in which to place samples of materials for determining their light and heat stability. These cabinets do not always provide satisfactory data for establishing light and heat sensitivity of materials due to uneven exposure over long periods of time, and improvements in cabinet design and function are necessary.

SUMMARY OF THE INVENTION

According to this invention, a sample chamber is provided in which artificial light sources are positioned and transparent and reflective materials are utilized in construction such that the test samples are each bathed or washed with light from every direction. The sample chambers of this invention can be stand-alone sample chambers or can be physically inserted or incorporated into existing commercial stability testing chambers. The stand-alone embodiments of the invention must of necessity have four supporting wall means in addition to top and bottom closure means. The insertable embodiments of the invention have front and back supporting wall means connecting the top and bottom closure means. Typical commercial cabinets with which the sample chamber of the invention can be usefully inserted are the Forma Scientific Incubator Model #3918 for temperature stability testing or Model #3940 for humidity stability testing. These models have reflective inner side walls with air circulation ports and when equipped with sample chambers of the invention provide in one unit, light, temperature and humidity data for the sample being tested so as to establish an accurate expiration date for the sample.

BRIEF DESCRIPTION OF THE DRAWINGS

In the drawings:

FIG. 2 is a partial sectional view of the stand-alone light stability embodiment of the invention taken along the vertical center axis or plane of FIG. 1 showing the side corner frame support channel members attached to the upper 5 and lower 3 closure members, the upper and lower bearing members for the cylindrical tube and the protuberance for holding the tube in place.

FIG. 3 is a cross-sectional view of supporting channel 11 to support walls 8 and 8' and to connect plate 3 to closure 5.

FIG. 4 is a top plan view of the base plate 3 showing bearing 13, protrusion 14 and openings 4 through protrusion 14.

FIG. 5 is a top plan view of closure 5 showing opening 6 therethrough for tube 1 and also showing bearing 12.

DESCRIPTION OF THE PREFERRED EMBODIMENT

Figure 1:
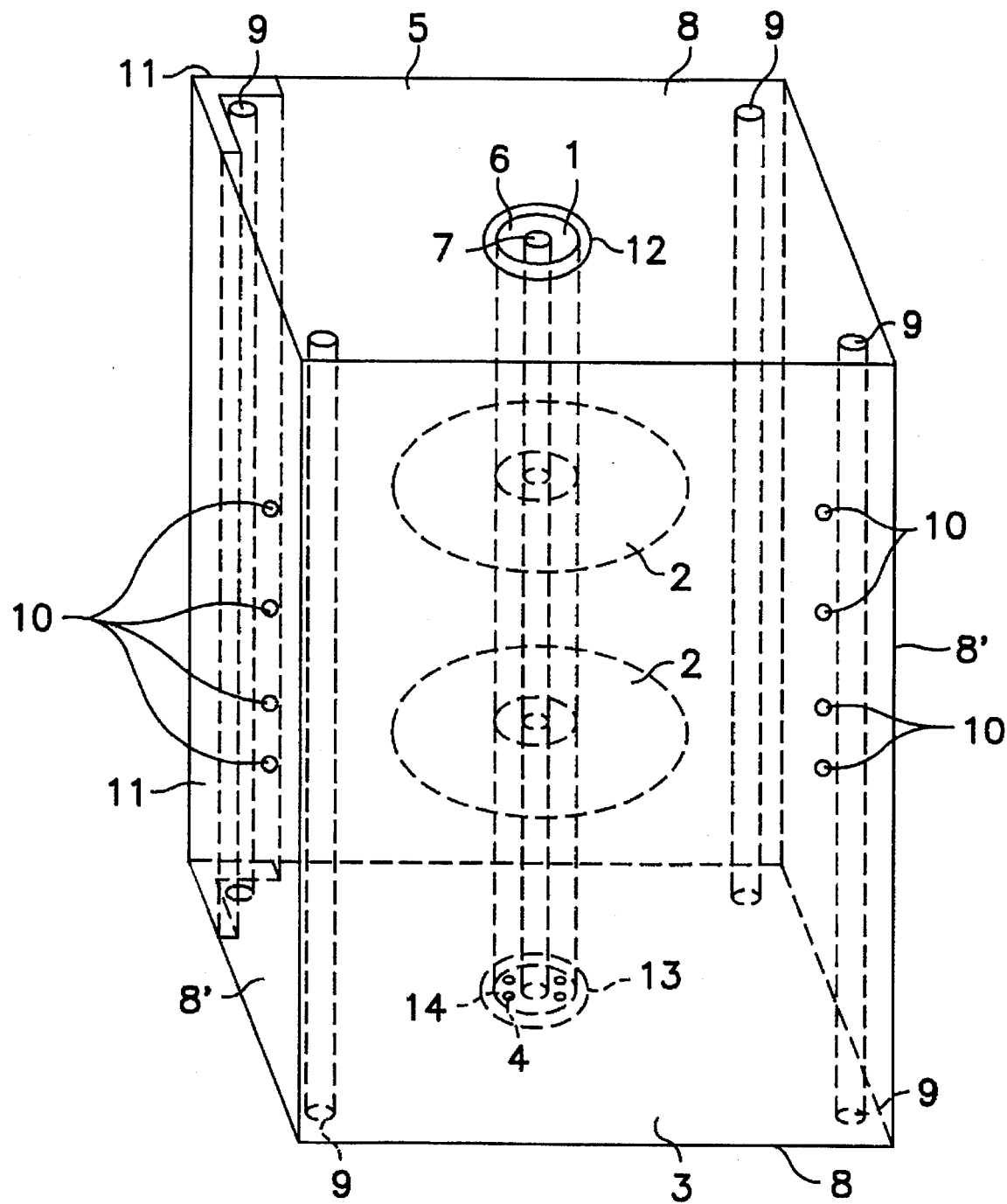
FIG 1 is a perspective view of the stand-alone light stability embodiment of the invention employing five light sources, having top, bottom and four enclosing and reflecting wall means and having all interior means transparent including rotatable shelf means, by way of example.

Referring to FIG. 1, a cylindrical hollow transparent tube 1 is centrally arranged in a sample chamber defined by a horizontally upwardly mirrored base plate 3, a downwardly mirrored closure 5 and inwardly mirrored vertical walls 8 and 8'. The base plate 3 has a plurality of cylindrical openings 4 extending through bearing 13 and protuberance 14 into tube 1 and the closure 5 has a cylindrical opening 6 for receiving tube 1 such that air can circulate through tube 1. Walls 8 and 8' are attached to base plate 3 and closure 5 at their respective peripheral edges. Tube I has a plurality of circular transparent horizontal shelves 2 mounted thereon in vertical spaced relationship to each other. The enclosed space or sample chamber defined by plate 3, closure 5 and walls 8 and 8' is sized to permit rotation of shelves 2. Walls 8' are provided with a plurality of small openings 10 therein to permit outside air circulation within the enclosed space or sample chamber.

Disposed within hollow tube 1 is artificial light source 7 extending substantially the full length of tube 1. Similarly hollow tube 1 is sized such that when light source 7 is disposed therein, sufficient space is provided between light source 7 and the inside surface of tube 1 to permit air circulation in tube 1 through openings 4 and 6.

Disposed within the enclosed space of the sample chamber are four artificial light sources 9 extending between plate 3 and closure 5 and parallel with tube 1. The artificial light sources 9 preferably are 4100 K fluorescent bulbs positioned such that, together with the light source 7 disposed within tube 1, at least 200 foot candles and preferably 400 foot candles of light are provided within the enclosed space or sample chamber. With these light sources and the reflected light from the mirrored surfaces, every part of a sample, for example, a pharmaceutical, on any of shelves 2 is washed in light. The center tube 1 is preferably made of clear plexiglass, the shelves 2 are preferably made from clear Lexan and the base plate 3, closure means 5 and vertical walls 8 and 8' are made from mirror coated Lexan.

Associated with the sample chamber of FIG. 1 but not shown in the drawing are external conventional electrical supply means and external conventional air circulation means.

Referring now to FIG. 2, back wall 8 is joined to stainless steel frame support channel 11, shown more clearly in FIG. 3. Although not shown for lack of space, channel 11 is present in each vertical corner of the sample cabinet. Also shown in FIG. 2, the upper section, is the tube 1 extending upwardly through cylindrical opening 6 and being held in place by circular bearing member 12. Further shown in FIG. 2, the lower section, is circular bearing 13 attached to base plate 3, upon which bearing, tube 6 rotates. Tube 6 is held in place on bearing 13 by circular protrusion 14 which is attached to bearing 13 and extends upwardly within tube 6. Openings 4 extend upwardly through plate 3, bearing 13 and protuberance 14. Referring again to FIG. 2, flange 15 is shown locking shelf 2 to tube 6. The bearing members 12 and 13 as well as circular protrusion 14 are preferably made from high density polyethylene. Angle irons 16 around the periphery of base plate 3 and at its midsection support base plate 3.

FIG. 3 shows in cross-section an angled channel 11 used to support walls 8 and 8', to connect base plate 3 to closure 5 and to support artificial lights 9.

FIG. 4 shows upwardly mirrored base plate 3 and is sized the same as downwardly mirrored closure 5 shown in FIG. 5. The bearing member 13 and circular protrusion 14 with openings 4 therethrough are shown in FIG. 4 and bearing member 12 is shown in FIG. 5.

In the embodiment of the invention for insertion into commercial cabinets, only the front and back walls 8 are necessary since such cabinets have mirrored interior side walls and vents for air circulation. Also the front wall 8 in all embodiments can be a door hinged to channel 11. Referring to FIG. 1, in such an embodiment side walls 8' would be omitted but channel 11 would be present in each vertical corner to connect the base plate 3 with the closure 5.

The artificial light sources 7 and 9 are preferably Sylvania or Phillips brands of fluorescent 4100 k light tubes. The dimensions of the embodiment of FIGS. 1 and 2 is about 4 feet in height, 30 inches in width and 26 inches in depth. In such a sized cabinet or chamber of this invention equipped with these light sources, the light throughout the chamber to which the samples are exposed will be at least 200 foot candles. If the samples are not placed on a shelf too close to each other, so as not to shade each other, the 200 foot candles of light will bathe each sample.

Modifications can be made in the apparatus of FIG. 1. For example, the base plate 3 and the closure 5 can each be circular, octagonal, etc. Also tube 1 can be sized large enough in diameter such that two or three fluorescent tubes can be fitted therein. Other modifications in structure may occur to those skilled in the art.

We claim:

1. In an apparatus for exposing samples to artificial light at a constant temperature such that the tops, bottoms and all sides of the samples are washed with light, an arrangement which comprises:

a) a cylindrical hollow transparent tubular means open at each end, b) a plurality of transparent horizontal shelf means mounted on the tubular means, c) the cylindrical hollow transparent tubular means being rotatably and vertically mounted on a horizontal upwardly mirrored base means having a plurality of cylindrical openings therethrough into the tubular means, d) the cylindrical hollow transparent tubular means having horizontally disposed at its upper end a downwardly mirrored closure means having a cylindrical opening sized to enclose the tubular means, e) at least one artificial light source disposed within and extending substantially the length of the tubular means, f) the horizontally disposed upwardly mirrored base means and the horizontally disposed downwardly mirrored closure means being connected at the peripheral edges thereof by vertical inwardly facing mirrored wall means defining an enclosed space, the space enclosed by the inwardly mirrored wall means being sized to permit rotation of the circular transparent horizontal shelf means, g) the inwardly facing mirrored wall means having a plurality of openings therein to provide air circulation within the enclosed space, h) and at least three artificial light sources substantially evenly disposed vertically within the said enclosed space and adjacent to the said inwardly mirrored vertical wall means.

2. The apparatus of claim 1 wherein the horizontally disposed upwardly mirrored base means and the horizontally disposed downwardly mirrored closure means are each rectangular and similarly sized.

3. The apparatus of claim 2 wherein the horizontally disposed upwardly mirrored base means and the horizontally disposed downwardly mirrored closure means are connected at each edge by the inwardly mirrored vertical wall means.

4. The apparatus of claim 3 having four artificial light sources vertically disposed, one at each vertical corner of the enclosed space.

5. The apparatus of claim 2 wherein the horizontally disposed upwardly mirrored base means and the horizontally disposed downwardly mirrored closure means are connected by only two oppositely facing inwardly mirrored vertical wall means.

6. The apparatus of claim 5 having four artificial light sources vertically disposed, one at each vertical corner of the enclosed space.

* * * * *